United States Patent [19]

Beriger

[11] 4,229,454
[45] Oct. 21, 1980

[54] INSECTICIDAL 5-PHENYLCARBAMOYL-BARBITURIC ACID

[75] Inventor: Ernst Beriger, Allschwil, Switzerland

[73] Assignee: Ciba-Geigy Corporation, Ardsley, N.Y.

[21] Appl. No.: 972,588

[22] Filed: Dec. 22, 1978

Related U.S. Application Data

[63] Continuation of Ser. No. 870,242, Jan. 17, 1978, abandoned, which is a continuation of Ser. No. 791,268, Apr. 27, 1977, abandoned.

[30] Foreign Application Priority Data

May 6, 1976 [CH] Switzerland ............ 5687/76
Nov. 3, 1976 [CH] Switzerland ............ 13850/76
Mar. 30, 1977 [CH] Switzerland ............ 3981/77

[51] Int. Cl.² .................................. C07D 239/62
[52] U.S. Cl. ........................... 424/254; 544/301
[58] Field of Search ................... 424/254; 544/301

[56] References Cited

U.S. PATENT DOCUMENTS 3,828,043 8/1974 Kay et al. ............... 424/254
3,961,061 6/1976 Kramer et al. .......... 424/254

FOREIGN PATENT DOCUMENTS 39-1445 2/1964 Japan ....................... 544/301

Primary Examiner—Paul M. Coughlan, Jr.
Attorney, Agent, or Firm—Frederick H. Rabin

[57] ABSTRACT

Compounds of the formula

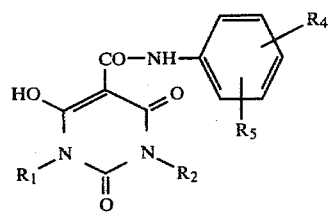

wherein $R_1$ is Methyl or ethyl, $R_2$ is $C_1$–$C_4$-alkyl or allyl, $R_4$ is halogen, methyl or trifluoromethyl and $R_5$ is hydrogen, halogen, methyl or trifluoromethyl and their tautomers exhibit valuable insecticidal properties.

23 Claims, No Drawings

INSECTICIDAL 5-PHENYLCARBAMOYL-BARBITURIC ACID

This is a continuation of application Ser. No. 870,242 filed on Jan. 17, 1978, which was a continuation of application Ser. No. 791,268 filed on Apr. 27, 1977, both now abandoned.

The present invention provides novel 5-phenylcarbamoyl-barbituric acids which act against insects, a process for their manufacture as well as insecticidal compositions which contain these compounds as active principle, and a method of controlling insects which comprises the use of the novel compounds.

The novel 5-phenylcarbamoyl-barbituric acids have the formula I

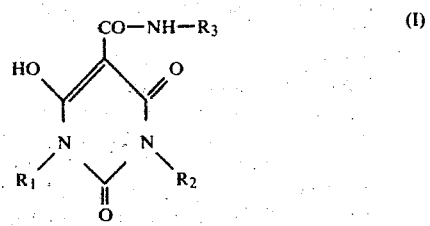

(I)

wherein
 $R_1$ represents a methyl or ethyl group,
 $R_2$ represents a $C_1$–$C_4$-alkyl or allyl group and
 $R_3$ represents a substituted phenyl group of the formula

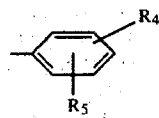

in which
 $R_4$ represents a halogen atom or a methyl or trifluoromethyl group and
 $R_5$ represents a hydrogen or halogen atom or a methyl or trifluoromethyl group.

By the term "halogen" are meant chlorine, fluorine, bromine and iodine atoms. Suitable $C_1$–$C_4$-alkyl groups are the methyl, ethyl, n-propyl, isopropyl, n-butyl, isobutyl, sec.-butyl and tert.-butyl group.

Particularly preferred compounds on account of their action against insects, chiefly against insects which are injurious to plants and animals, are those of the formula I wherein
 $R_4$ represents a chlorine, bromine or iodine atom or a trifluoromethyl group, and
 $R_5$ represents a hydrogen, chlorine, bromine or iodine atom or a methyl or trifluoromethyl group.

Compounds having a particularly good insecticidal action are those of the formula I wherein $R_3$ represents a 4-chlorophenyl, 4-bromophenyl, 4-iodophenyl, 2,4-dichlorophenyl, 3,4-dichlorophenyl, 3-trifluoromethylphenyl, 4-trifluoromethylphenyl, 3,5-bis-trifluoromethylphenyl, 3-chloro-4-tri-fluoromethylphenyl, 4-chloro-3-trifluoromethylphenyl or 4-chloro-2-methylphenyl group.

Compounds of the present invention wherein
 (i) $R_2$ represents a methyl, ethyl or isopropyl group, and
 (ii) $R_2$ represents an isobutyl or allyl group, constitute further preferred subgroups.

The compounds of the formula I, which are in themselves novel, are obtained by methods which are known per se, for example by (a) reacting an ester of the formula II

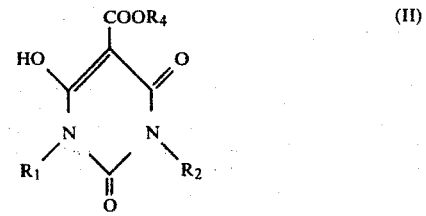

(II)

with an aniline of the formula III

$R_3$—$NH_2$ (III);

(b) reacting a compound of the formula IV

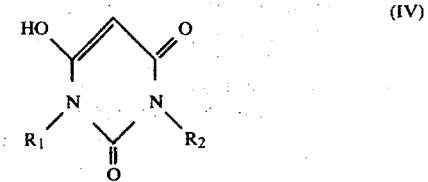

(IV)

with an isocyanate of the formula V

$R_3$—N=C=O (V);

or (c) treating a compound of the above formula IV with an azide of the formula VI

$R_3$—CO—$N_3$ (VI).

In the above formulae (II) to (VI), the symbols $R_1$ to $R_3$ have the meanings assigned to them in formula I and $R_4$ represents a $C_1$–$C_4$-alkyl group.

Preferably, processes (a) and (c) are carried out at a reaction temperature between 0° and 200° C. The reactions can be carried out under normal or elevated pressure, optionally in a solvent or diluent which is inert to the reactants and optionally in the presence of a base.

Examples of solvents or diluents which are suitable for these reactions are: ether and ethereal compounds, such as dipropyl ether, dioxan, dimethoxyethane and tetrahydrofuran; amides, such as N,N-dialkylated carboxamides; aliphatic, aromatic and halogenated hydrocarbons, in particular toluene, xylenes and chlorobenzene; nitriles, such as acetonitriles; dimethyl sulphoxide; and ketones, such as actone and methyl ethyl ketone.

Suitable bases are in particular tertiary amines, such as triethylamine, dimethyl aniline, pyridine, picolines and lutidines; also hydroxides, oxides, carbonates and bicarbonates of alkali metals and alkaline earth metals, for example potassium tert.-butylate and sodium methylate.

The starting materials of the formulae II to VI are known (see for example "Chem. Ber.," 54, 1038 [1929]) or they can be prepared in a manner analogous to that employed for obtaining the known compounds.

The compounds of the present invention exist in various tautomeric forms (keto/enol). The invention is also to be understood as comprising the individual tautomers and mixtures thereof.

Surprisingly, it has now been found that the compounds of the formula I have an effective insecticidal action, in particular against insects which are injurious to plants and animals. These compounds act, for example, against eggs, larvae, nymphs, pupae, and adults of insects of the families:

| order Colleoptera | { Anobiidae, Bostrichidae, Bruchidae, Chrysomelidae, Cleridae, Curculionidae, Dermestidae, Elateridae, Ipidae, Lathridiidae, Nitidulidae, Ptinidae, Cucujidae, Scarabaeidae and Tenebrionidae; |
|---|---|
| order Diptera | { Agromycidae, Anthomyiidae, Calliphoridae, Cecidomyiidae, Chloropidae, Gastrophilidae, Hippoboscidae, Hypodermidae, Muscidae, Stomoxydae, Tabanidae, Tipulidae and Trypetidae; | and also of the families: Noctuidae and Pyralidae (order Lepidoptera).

The compounds of the formula I are suitable chiefly for controlling plant pests of the order Colleoptera, especially of the families Chrysomelidae and Curculionidae (for example *Leptinotarsa decemlineata* and *Anthonomous grandis*) as well as for controlling ectoparasitic insects of the family Calliphoridae, in particular of the genus Lucilia (for example *Lucilia sericata*). Accordingly, the use of the compounds of the present invention for treating cotton and fruit crops and for the external treatment of productive livestock and their environment is to be highlighted.

The insecticidal action can be substantially broadened and adapted to given circumstances by the addition of other pesticides (for example insecticides and acaricides). Examples of suitable additives include: organic phosphorus compounds, nitrophenols and derivatives thereof, formamidines, ureas, pyethroids, ureas, carbamates, and chlorinated hydrocarbons.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dusts, emulsifiable concentrates, granules, dispersions, sprays, to solutions, or suspensions, in the conventional formulation which is commonly employed in application technology.

The compositions according to the invention are manufactured in known manner by homogeneously mixing and/or grinding active substances of the formula I with the suitable carriers, with or without the addition of dispersants or solvents which are inert to the active substances.

The active substances may be processed to the following formulations:
  Solid formulations:
  Dusts, tracking agents and granules (coated granules, impregnated granules and homogeneous granules).
  Liquid formulations:
  (a) active substances which are dispersible in water: wettable powders, pastes and emulsions;
  (b) solutions.

The content of active substance in the above described compositions is between 0.1% and 95%, though higher concentrations can also be used if the compositions are applied from an aircraft or other appropriate application devices.

The active substances of the formula I can, for example, be formulated as follows (throughout the present specification all parts and percentages are by weight):
Dusts
The following substances are used to manufacture (a) a 5% and (b) a 2% dust:
  (a) 5 parts of active substance, 95 parts of talc;
  (b) 2 parts of active substance, 1 part of highly disperse silicic acid, 97 parts of talc.

The active substances are mixed with the carriers and ground.
Granules
The following substances are used to produce 5% granules:
  5 parts of active substance,
  0.25 parts of epichlorohydrin,
  0.25 parts of cetyl polyglycol ether,
  3.50 parts of polyethylene glycol,
  91 parts of kaolin (particle size 0.3–0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.
Wettable powder:
The following constituents are used for the preparation of (a) a 40%, (b) and (c) a 25%, and (d) a 10% wettable powder:
  (a) 40 parts of active substance,
    5 parts of sodium ligninsulphonate,
    1 part of sodium dibutylnaphthalenesulphonate,
    54 parts of silicic acid.
  (b) 25 parts of active substance,
    4.5 parts of calcium ligninsulphonate,
    1.9 parts of Champagne chalk/hydroxyethyl cellulose mixture (1:1),
    1.5 parts of sodium dibutylnaphthalenesulphonate,
    19.5 parts of silicic acid,
    19.5 parts of Champagne chalk,
    28.1 parts of kaolin,
  (c) 25 parts of active substance,
    2.5 parts of isooctylphenoxy-polyoxyethyleneethanol,
    1.7 parts of Champagne chalk/hydroxyethyl cellulose mixture (1:1),
    8.3 parts of sodium aluminium silicate,
    16.5 parts of kieselguhr,
    46 parts of kaolin,
  (d) 10 parts of active substance,
    3 parts of a mixture of the sodium salts of saturated fatty alcohol sulphates,
    5 parts of naphthalenesulphonic acid/formaldehyde condensate,
    82 parts of kaolin.

The active substances are homogeneously mixed, in suitable mixers, with the additives, the mixture being then ground in the appropriate mills and rollers. Wettable powders are obtained which can be diluted with water to give suspensions of the desired concentration.
Emulsifiable concentrates:
The following substances are used to produce (a) a 10% and (b) a 25% emulsifiable concentrate:
  (a) 10 parts of active substance, 3.4 parts of epoxidised vegetable oil,
3.4 parts of a combination emulsifier consisting of fatty alcohol polyglycol ether and alkylarylsulphonate calcium salt,
40 parts of dimethyl formamide,
43.2 parts of xylene;
(b) 25 parts of active substance,
2.5 parts of epoxidised vegetable oil,
10 parts of alkylarylsulphonate/fatty alcohol polyglycol ether mixture,
5 parts of dimethyl formamide,
57.5 parts of xylene.

By diluting these concentrates with water it is possible to obtain emulsions of the required concentration.
Spray:
The following ingredients are used to prepare (a) a 5% spray.
(a) 5 parts of active substance,
1 part of epichlorohydrin,
94 parts of ligroin (boiling range 160°–190° C.).

The invention is further illustrated by the following Examples.

EXAMPLE 1

Preparation of 5-(4-chlorophenyl)-carbamoyl-1,3-dimethylbarbituric acid

To a solution of 15.6 g of 1,3-dimethylbarbituric acid in 150 ml of dimethyl sulphoxide were added dropwise 10.1 g of triethylamine at a temperature of 20° to 30° C. and with continual stirring, and thereafter 15.6 g of 4-chlorophenylisocyanate, dissolved in a small amount of dimethyl sulphoxide. The reaction mixture was stirred for a further 24 hours at room temperature and then poured into a solution of 15 ml of conc. hydrochloric acid in 350 ml of water. The resultant condensation product was collected with suction and recrystallised from dioxan, giving the compound of the formula (compound 1)

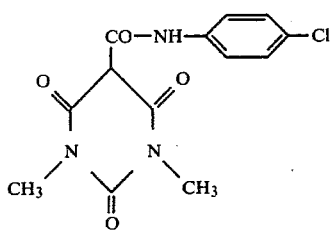

with a melting point of 225°–227° C.

The following compounds of the formula Ia can be obtained in analogous manner

| Compound | $R_1$ | $R_2$ | $R_4$ | $R_5$ | m.p. (°C.) |
|---|---|---|---|---|---|
| 2 | $CH_3$ | $CH_3$ | 2-Cl | 4-Cl | 208–210 |
| 3 | $CH_3$ | $CH_3$ | 3-$CF_3$ | 4-Cl | 180–182 |
| 4 | $CH_3$ | $CH_3$ | 4-$CF_3$ | H | 188–190 |
| 5 | $CH_3$ | $CH_3$ | 3-$CF_3$ | H | 139–141 |
| 6 | $CH_3$ | $CH_3$ | 3-$CF_3$ | 5-$CF_3$ | 184–185 |
| 7 | $CH_3$ | $CH_3$ | 4-Br | H | 243–245 |
| 8 | $CH_3$ | $CH_3$ | 4-I | H | 254–255 |
| 9 | $CH_3$ | $CH_3$ | 4-F | H | 188–190 |
| 10 | $CH_3$ | $CH_3$ | 3-Cl | 4-Cl | 205–206 |
| 11 | $CH_3$ | $CH_3$ | 4-Cl | 2-$CH_3$ | 179–180 |
| 12 | $CH_3$ | $CH_3$ | 2-Cl | 5-$CF_3$ | 212–213 |
| 13 | $CH_3$ | $CH_3$ | 3-Cl | 4-$CF_3$ | 160–161 |
| 14 | $CH_3$ | $CH_3$ | $CH_3$ | H | 176–179 |
| 15 | $CH_3$ | $C_2H_5$ | 3-$CF_3$ | 4-Cl | 124–126 |
| 16 | $CH_3$ | $C_2H_5$ | 4-Br | H | 193–195 |
| 17 | $CH_3$ | $C_2H_5$ | 2-Cl | 4-Cl | 133–135 |
| 18 | $CH_3$ | $C_2H_5$ | 3-$CF_3$ | H | 116–118 |
| 19 | $CH_3$ | (i)-$C_3H_7$ | 4-Cl | H | 183–185 |
| 20 | $CH_3$ | (i)-$C_3H_7$ | 2-Cl | 4-Cl | 163–166 |
| 21 | $CH_3$ | (i)-$C_3H_7$ | 4-Br | H | 183–185 |
| 22 | $CH_3$ | (i)-$C_4H_9$ | 4-Br | H | 156–157 |
| 23 | $CH_3$ | (i)-$C_4H_9$ | 2-Cl | 4-Cl | 157–158 |
| 24 | $CH_3$ | (i)-$C_4H_9$ | 3-$CF_3$ | H | 100–102 |
| 25 | $CH_3$ | (i)-$C_4H_9$ | 4-$CF_3$ | H | 115–117 |
| 26 | $CH_3$ | $CH_2=CH-CH_2-$ | 4-Br | H | 124–125 |
| 27 | $CH_3$ | $CH_2=CH-CH_2-$ | 2-Cl | 4-Cl | 143–145 |
| 28 | $CH_3$ | $CH_2=CH-CH_2-$ | 3-$CF_3$ | H | 106–108 |
| 29 | $CH_3$ | $CH_2=CH-CH_2-$ | 4-$CF_3$ | H | 109–111 |
| 30 | $C_2H_5$ | $C_2H_5$ | 4-Cl | H | 164–166 |
| 31 | $C_2H_5$ | $C_2H_5$ | 2-Cl | 4-Cl | 143–144 |
| 32 | $C_2H_5$ | $C_2H_5$ | 4-Br | H | 170–172 |
| 33 | $C_2H_5$ | $C_2H_5$ | 4-$CF_3$ | H | |
| 34 | $C_2H_5$ | $C_2H_5$ | 3-$CF_3$ | 5-$CF_3$ | |

EXAMPLE 2

Insecticidal stomach poison action: *Leptinotarsa decemlineata*

Potato plants are sprayed with a 0.05% aqueous emulsion of the compound to be tested (obtained from a 10% emulsifiable concentrate).

After the spray coating had dried, the plants were populated with larvae of Leptinotarsa decemlineata in the $L_3$-stage. Two plants were used per test substance and evaluation of mortality was made after 2, 4, 8, 24 and 48 hours. The test was carried out at 24° C. and 60% relative humidity.

In the above test, compounds of Example 1 exhibited good insecticidal stomach poison action against larvae of the species Leptinotarsa decemlineata.

EXAMPLE 3

Insecticidal stomach poison action: *Spodoptera littoralis*

The method described in Example 2 was repeated using cotton plants instead of potato plants and larvae of the species Spodoptera littoralis in the $L_3$-stage instead of Leptinotarsa decemlineata larvae.

In this test, particularly compounds 3, 5, 6 and 7 displayed good action against Spodoptera littoralis.

EXAMPLE 4

Insecticidal stomach poison/contact action: *Anthanomus grandis*

Cotton plants in pots were sprayed with a spray broth containing 500 ppm of test substance (obtained from a 25% wettable powder) and allowed to dry. Each of the plants was then populated with 5 one-day-old insects of the species Anthanomus grandis and the plants were kept in greenhouse compartments at 24° C. and 60% relative humidity.

The number of dead and moribund insects was determined at intervals of 2, 4, 24 and 48 hours respectively after the start of the test. Two plants were used per test substance.

In the above test particularly, the compounds of Example 1 exhibited a very good action against Anthanomus grandis.

EXAMPLE 5

Action against *Chilo suppressalis*

Rice seedlings of the variety Caloro were reared in plastic pots (6 seedlings per pot) so that their roots became matted to a disc. The roots were then immersed in a 0.8% solution of the active compound to be tested. Then each pot was populated with 5 Chilo suppressalis larvae in the $L_2$-stage and the treated plants were subsequently replaced in the pots on top of the larvae.

Evaluation of mortality was made after 5 days and the test was carried out at 24° C. and 70% relative humidity.

In this test, compounds 1, 3, 4, 7, 8, 10, 13, 20 and 21 of Example 1 exhibited a positive action against Chilo suppressalis.

EXAMPLE 6

Action on *Lucilia sericata*

2 ml of an aqueous solution containing 1, 2, 4, 8 or 16 ppm of the compound to be tested was added to 2 ml of a culture medium. Approx. 30 freshly hatched-out larvae of Lucilia sericata were then added to the culture medium and the insecticidal action was determined after 96 hours by evaluating the mortality rate.

In this test, the compounds of Example 1, especially compounds 1 to 10, 15 to 17, 19, 21 and 30 to 32, acted well against larvae of Lucilia sericata.

EXAMPLE 7

Inhibitory action against damage by eating: *Leptinotarsa decemlineata*

Two potato plants with a height of 15 cm were sprayed with 25 ml of an acetone/water mixture (1:1) containing 0.05% of test substance.

After the spray coating had dried, each of the potato plants was populated with 10 larvae of the species Leptinotarsa decemlineata ($L_3$-stage). A plastic cylinder was then slipped over each plant to prevent the larvae from migrating.

A copper gauze top was used to seal the cylinder. The damage caused by eating was determined 2 days later.

In the above test, the compounds, 4, 6, 7, 8, 13 and 31 of Example 1 effectively inhibited damage from eating caused by larvae of the species Leptinotarsa decemlineata.

EXAMPLE 8

Inhibitory action against damage by eating: *Spodoptera littoralis*

Two cotton plants with a height of 15 cm were sprayed with 25 ml of a solution of acetone/water (1:1) containing 0.1% of test substance. After the spray coating had dried, each plant was populated with 5 larvae of the species Spodoptera littoralis ($L_3$-stage). A plastic cylinder was slipped over each plant and sealed with a copper gauze top. The damage caused by eating was determined 2 days later.

In the above test, the compounds 4, 6, 7, 8, 13 and 31 of Example 1 inhibited damage from eating caused by larvae of the species Spodoptera littoralis.

EXAMPLE 9

Action against *Musca domestica*

50 g of freshly prepared CSMA nutrient substrate for maggots were charged into beakers and subsequently 5, 2.5 and 0.5 ml respectively of a 1% acetonic solution of the compound to be tested was pipetted onto the nutrient substrate present in the beakers. The substrate was then thoroughly mixed and the acetone subsequently allowed to evaporate over a period of at least 20 hours.

Then 25 one day-old maggots of Musca domestica were put into each of the beakers containing the treated nutrient substrate for testing with each active substance at one of its given concentrations. After the maggots had pupated, the pupae were separated from the substrate by flushing them out with water and then deposited in containers closed with a perforated top.

Each batch of flushed out pupae was counted to determine the toxic effect of the active substance on the maggot development. The number of flies which had hatched out of the pupae was then counted after 10 days and any influence on the metamorphosis thereby determined.

In the above test, the compounds of Example 1 displayed a position action against Musca domestica.

EXAMPLE 10

Action against *Aedes aegypti* larvae

Active substance concentrations of 10, 5 and 1 ppm respectively were obtained by pipetting a specific amount of a 0.1% solution of the active substance in acetone onto the surface of 150 ml of water in each of a number of beakers. After the acetone had evaporated, 30 to 40 two-day-old larvae of Aedes aegypti were put into each of the beakers containing the active substance solution. Two beakers per concentration of active substance were used for the test. Then ground feed was added to the beakers, which were covered with a copper gauze top.

Evaluation of mortality was made after 1, 2 and 5 days respectively. Subsequently, evaluation was made of the inhibiting action on pupation, metamorphosis, and shedding and emergence to the adult stage.

In this test, the compounds 1, 2, 6, 7, 8, 10, 13, 20 and 31 of Example 1 displayed good action against Aedes aegypti larvae.

What is claimed is:
1. 5-(4-Chlorophenyl)-carbamoyl-1,3-dimethyl-barbituric acid.
2. 5-(2,4-Dichlorophenyl)-carbamoyl-1,3-dimethyl-barbituric acid.
3. 5-(4-Chloro-3-trifluoromethylphenyl)-carbamoyl-1,3-dimethyl-barbituric acid.
4. 5-(4-Trifluoromethylphenyl)-carbamoyl-1,3-dimethyl-barbituric acid.
5. 5-(3,5-Bis-trifluoromethylphenyl)-carbamoyl-1,3-dimethyl-barbituric acid.
6. 5-(4-Bromophenyl)-carbamoyl-1,3-dimethyl-barbituric acid.
7. 5-(4-Iodophenyl)-carbamoyl-1,3-dimethyl-barbituric acid.
8. 5-(4-Fluorophenyl)-carbamoyl-1,3-dimethyl-barbituric acid.
9. 5-(4-Chlorophenyl)-carbamoyl-1,3-diethyl-barbituric acid.
10. 5-(4-Bromophenyl)-carbamoyl-1,3-diethyl-barbituric acid.

11. 5-(4-Bromophenyl)-carbamoyl-1-methyl-3-isopropyl-barbituric acid.

12. 5-(4-Trifluoromethylphenyl)-carbamoyl-1,3-diethyl-barbituric acid.

13. 5-(3,5-Bistrifluoromethylphenyl)-carbamoyl-1,3-diethyl-barbituric acid.

14. 5-(3-Trifluoromethylphenyl)-carbamoyl-1,3-dimethyl-barbituric acid.

15. 5-(2,4-Dichlorophenyl)-carbamoyl-1,3-diethyl-barbituric acid.

16. 5-(4-Chloro-3-trifluoromethylphenyl)-carbamoyl-1-methyl-3-ethyl-barbituric acid.

17. 5-(2,4-Dichlorophenyl)-carbamoyl-1-methyl-3-ethyl-barbituric acid.

18. A method of controlling insect pests at a locus, which method comprises applying to said locus an insecticidally effective amount of a compound selected from the group consisting of: 5-(4-chlorophenyl)-carbamoyl-1,3-dimethyl-barbituric acid; 5-(2,4-dichlorophenyl)-carbamoyl-1,3-dimethyl-barbituric acid; 5-(4-chloro-3-trifluoromethylphenyl)-carbamoyl-1,3-dimethyl-barbituric acid; 5-(4-trifluoromethylphenyl)-carbamoyl-1,3-dimethyl-barbituric acid; 5-(3,5-bis-trifluoromethylphenyl)-carbamoyl-1,3-dimethyl-barbituric acid; 5-(4-bromophenyl)-carbamoyl-1,3-dimethyl-barbituric acid; 5-(4-iodophenyl)-carbamoyl-1,3-dimethyl-barbituric acid; 5-(4-fluorophenyl)-carbamoyl-1,3-dimethyl-barbituric acid; 5-(4-chlorophenyl)-carbamoyl-1,3-diethyl-barbituric acid; 5-(4-bromophenyl)-carbamoyl-1,3-diethyl-barbituric acid; 5-(4-bromophenyl)-carbamoyl-1-methyl-3-isopropylbarbituric acid; 5-(4-trifluoromethylphenyl)-carbamoyl-1,3-diethyl-barbituric acid; 5-(3,5-bis-trifluoromethylphenyl)-carbamoyl-1,3-diethyl-barbituric acid; 5-(3-trifluoromethyl-phenyl)-carbamoyl-1,3-dimethyl-barbituric acid; 5-(2,4-dichlorophenyl)-carbamoyl-1,3-diethyl-barbituric acid; 5-(4-chloro-3-trifluoromethylphenyl)-carbamoyl-1-methyl-3-ethyl-barbituric acid; and 5-(2,4-dichlorophenyl)-carbamoyl-1-methyl-3-ethyl-barbituric acid.

19. A method according to claim 18 wherein the insect pests are ectoparasitic insects of the genus Lucilia.

20. A method according to claim 19 wherein the insect pests are ectoparasitic insects of the species Lucilia sericata.

21. A method according to claim 18 which compund is 5-(4-chlorophenyl)-carbamoyl-1,3-dimethyl-barbituric acid.

22. The method according to claim 18 in which the compound is 5-(4-chloro-3-trifluoromethylphenyl)-carbamoyl-1,3-dimethyl-barbituric acid.

23. The method according to claim 18 in which the compound is 5-(4-trifluoromethylphenyl)-carbamoyl-1,3-dimethyl-barbituric acid.

* * * * *